US012644091B2

(12) United States Patent
Zantl et al.

(10) Patent No.: US 12,644,091 B2
(45) Date of Patent: Jun. 2, 2026

(54) METHOD FOR CULTURING CELLS

(71) Applicant: ibidi GmbH, Gräfelfing (DE)

(72) Inventors: Roman Zantl, Gräfelfing (DE); Zeno Von Guttenberg, Gräfelfing (DE); Nina Baumann, Gräfelfing (DE); Moriz Walter, Wangen im Allgäu (DE); Andrea Traube, Nürtingen (DE)

(73) Assignee: ibidi GmbH, Gräfelfing (DE)

( * ) Notice: Subject to any disclaimer, the term of this patent is extended or adjusted under 35 U.S.C. 154(b) by 1381 days.

(21) Appl. No.: 17/184,800

(22) Filed: Feb. 25, 2021

(65) Prior Publication Data

US 2021/0269761 A1 Sep. 2, 2021

(30) Foreign Application Priority Data

Feb. 28, 2020 (EP) .................................... 20160085

(51) Int. Cl.
  *C12M 1/00* (2006.01)
  *C12M 1/26* (2006.01)
  (Continued)

(52) U.S. Cl.
  CPC ............ *C12M 41/48* (2013.01); *C12M 29/00* (2013.01); *C12M 29/20* (2013.01); *C12M 33/00* (2013.01); *C12M 41/36* (2013.01)

(58) Field of Classification Search
  CPC ...... C12M 23/16; C12M 23/20; C12M 23/22; C12M 23/34; C12M 23/40; C12M 29/00;
  (Continued)

(56) References Cited

U.S. PATENT DOCUMENTS

2011/0159522 A1* 6/2011 Kamm ............... G01N 33/5029
                                                              435/287.1
2014/0287451 A1 9/2014 McFetridge
                  (Continued)

FOREIGN PATENT DOCUMENTS

EP 2330181 B1 11/2018
EP 3581642 A1 12/2019
WO 2020018725 A1 1/2020

OTHER PUBLICATIONS

Extended European Search Report, European Patent Application No. 20160085.5, Aug. 14, 2020.

*Primary Examiner* — Lydia Edwards
(74) *Attorney, Agent, or Firm* — Lowenstein Sandler LLP

(57) ABSTRACT

The invention refers to a method for culturing cells. The cells are cultured in a substrate, wherein in the substrate a fluid channel system is formed, comprising a culturing channel having a culturing access to the outside, a storage channel having a storage access to the outside, and a transfer channel having a transfer access to the outside, wherein the culturing channel and the storage channel are fluidically connected to each other via the transfer channel. The method comprises supplying an initial cell suspension through the culturing access into the culturing channel or through the transfer access via the transfer channel into the culturing channel, growing a cell culture in the culturing channel, transferring cells of the cell culture from the culturing channel into the storage channel via the transfer channel, wherein the transfer is carried out by supplying a transfer liquid through the culturing access and transporting the transfer liquid through the culturing channel and the transfer channel into the storage channel, and storing and/or concentrating and/or homogenizing and/or diluting a cell suspension containing the transferred cells in the storage channel.

38 Claims, 9 Drawing Sheets

(51) Int. Cl.
 *C12M 1/34* (2006.01)
 *C12M 1/36* (2006.01)

(58) Field of Classification Search
 CPC ...... C12M 29/18; C12M 29/20; C12M 33/00;
  C12M 41/00; C12M 41/36; C12M 41/48;
  C12M 47/04; B03C 1/01; B03C 1/32;
  B03C 2201/18
 See application file for complete search history.

(56) References Cited

U.S. PATENT DOCUMENTS

| | | |
|---|---|---|
| 2016/0326476 A1 | 11/2016 | Maisch et al. |
| 2017/0067009 A1 | 3/2017 | Sloane et al. |

\* cited by examiner

METHOD FOR CULTURING CELLS

CROSS REFERENCE TO RELATED APPLICATIONS

The present application claims priority to European Patent Application No. 20 160 085.5, filed Feb. 28, 2020, which is incorporated herein by reference in its entirety.

The invention refers to a method for culturing cells.

For culturing cells, cells are seeded, a cell culture is grown by multiplying the cells, and subsequently the cells in the cell culture are further used, usually followed by concentration, homogenization, and/or dilution of a suspension of the grown cells. The grown cells can then be reseeded or removed from the system for further use in the laboratory.

Regarding the quality of the cells obtained by culturing it is significant that the process is carried out under conditions that are as sterile as possible and that the individual steps take place at appropriate points in time, since otherwise cells will be poorly supplied and may die if cell multiplication is not interrupted on time and the older cells are no longer adequately supplied, for example.

Therefore, it is desirable to provide a process that does not necessarily require the presence and participation of a human to carry out the respective process steps. In this respect, systems are known in which various containers connected by hoses are provided, in each of which a process step takes place, with valves being provided between the liquid containers which, together with pumps, enable liquids to be transported between the containers so that the process can take place at least partially without human intervention in the system.

In various aspects the described procedure is not ideal in handling. For example, a relatively complex modification is required if the containers in which cells are cultured, processed or stored are to be replaced. However, frequent replacement allows for better cell quality. In addition measures are required to keep the system in which the cells of the cell culture are cultured, processed, stored and transported sterile. It is therefore an object of the invention to provide a method for culturing cells that allows better handling.

The object is achieved by the subject matter of claim 1. Accordingly, the cells are cultured in a substrate, wherein in the substrate a fluid channel system is formed, comprising a culturing channel having a culturing access to the outside, a storage channel having a storage access to the outside, and a transfer channel having a transfer access to the outside, wherein the culturing channel and the storage channel are fluidically connected to each other via the transfer channel. The method comprises supplying an initial cell suspension through the culturing access into the culturing channel or through the transfer access via the transfer channel into the culturing channel, growing a cell culture of the initial cell suspension in the culturing channel, transferring cells of the cell culture from the culturing channel into the storage channel via the transfer channel, wherein transferring is carried out by supplying a transfer liquid through the culturing access and transporting the transfer liquid through the culturing channel and the transfer channel into the storage channel, and storing and/or concentrating and/or homogenizing and/or diluting a cell suspension containing the transferred cells in the storage channel.

It is obvious that the essential process steps all take place in the substrate. Thus, there are no separate processing containers. Replacement of all processing areas can simply be carried out by replacing the substrate used, with fewer steps required than in the known system because only one element is replaced instead of a plurality of processing containers and connections need only to be reestablished at the one substrate instead of a plurality of processing containers. In particular, there is no need to disconnect and reestablish connections between processing areas. Thus, this reduces the time required, without increasing the cost since no active components such as pumps or valves need to be replaced. Also, it is sufficient to replace one element, namely the substrate, by a new one and there is no need to acquire a plurality of new elements. In addition, it is comparatively easy to keep a system sterile, that is closed except for the accesses in a substrate.

In the following, the culturing channel, the transfer channel and the storage channel are referred to in part in simplified form by the general term "fluid channels" or "channels". Similarly, in the following, the culturing access, the transfer access and the storage access are referred to in simplified form by the general term "accesses". In addition, where a distinction is not necessary, the liquids involved in the process, for example cell suspension, transfer liquid, dilution liquid or flushing liquid, are referred to in the following in a simplified manner in part by the general term "liquid" or "liquids".

The substrate may be one of the substrates according to the invention described below. The substrate may be suitable for optical inspection of cells located in the substrate. In particular, the substrate may be a flat substrate that is transparent in the areas to be inspected. In particular, the substrate may be configured as a microscopy carrier. This is advantageous because optical inspections can be carried out before, during and/or after the culturing process, for example the quantity and properties of the cells or cell cultures can be inspected without removing cells. Removing the cells for inspections would falsify the results, and some inspections are only possible in the substrate. Thus, a more precise monitoring of the culturing process can be made possible.

The accesses allow supplying and discharging of liquids and the application of pressure. The accesses may be understood as inlets and outlets of the substrate, especially of the respective channel.

Here, the term "to the outside" is used to refer to the area outside the substrate. The term "access to the outside" indicates that the access is not an access via another channel of the fluid channel system or another structure inside the substrate. The access is a direct connection of the channel to the environment of the substrate. For example, the access may be an opening in one of the surfaces of the substrate.

The culturing channel is opened at both ends, with one end opened towards the transfer channel and one end opened towards the outside. The storage channel is opened to the outside at least at one end and also has a connection to the transfer channel. The connection may be but does not have to be located at the other end of the storage channel.

In particular, growing a cell culture is carried out by multiplying the cells in the culturing channel. The culturing channel may have a growth surface on which the first cell culture is growing. The culturing channel can thus be regarded as a growth channel.

The method may comprise transporting the liquid of the initial cell suspension out of the culturing channel particularly from the fluid channel system, while the cells are located in the culturing channel, i.e. after the initial cell suspension has been supplied. Discharging may be carried out such that the cells remain in the culturing channel. In particular, this can be achieved by delaying discharging after the cells have settled on the floor of the culturing channel and if necessary adhere thereto.

The method may comprise supplying a nutrient liquid particularly through the culturing access into the culturing channel or through the transfer access via the transfer channel into the culturing channel. In particular, supplying the nutrient liquid may be carried out during growing the cell culture. Optionally, the method may comprise subsequent discharging the nutrient liquid from culturing channel, particularly discharging from the fluid channel system. Supplying and discharging may each be carried out such that the cells remain in the culturing channel. Supplying and discharging the nutrient liquid may be carried out repeatedly during growing. In this way, a good supply of nutrients to the cells of the cell culture can be ensured.

Diluting a cell suspension, particularly the cell suspension containing the transferred cells, may comprise that a liquid is transported through the fluid channel in which the cell suspension is located, for example through the storage channel, and when transporting the liquid out of the fluid channel a portion of the cells remains in the fluid channel and another portion of the cells together with liquid is transported out of the fluid channel, particularly out of the substrate. For example, dilution in the storage channel and/or in the transfer channel and/or optionally after transferring the cells from the storage channel to a second culturing channel, may be carried out prior to growing a second cell culture in the second culturing channel.

Concentrating a cell suspension, particularly the cell suspension containing the transferred cells, may comprise that cells are retained in a channel, for example the storage channel, while transporting liquid out of the channel. When concentration is carried out in the storage channel, for example a semi-permeable membrane may be arranged at one of the accesses of the storage channel. Concentration may alternatively be carried out in the respective culturing channel. Then, for example a semi-permeable membrane may be arranged at the access of the culturing channel. Alternatively or in addition to providing a membrane, the floor of the substrate may have, in the area where concentration has to be carried out, for example in the storage channel, a structuring that retains cells. For example, the structures may have a saw tooth profile. Alternatively or additionally, the liquid can be transported at a sufficiently low flow velocity that is selected such that cells are not washed away.

Homogenization of a cell suspension, particularly the cell suspension containing the transferred cells, may comprise mixing the cell suspension by a movement of the cell suspension, for example an oscillating movement. This may be effected by applying suitable pressures.

In the method mentioned above all method steps in which liquids are moved in the fluid channel system may be carried out by means of active elements arranged exclusively outside the substrate.

Removing cells from the system may be carried out via a fluidic outlet from the substrate. A portion of the cells can be removed so that the cell culture in the substrate can be maintained with the remaining cells. In this way, cells are available in the laboratory for extended periods of time with consistent quality. In contrast, the process steps may also be optimized such that the largest possible quantity of cells is available at a single point in time, which are then completely removed from the system.

In particular, the steps may be carried out automatically by driving the active elements. This enables a plurality of method steps to be carried out in succession without requiring human intervention to initiate the respective following process step. In particular, also no direct intervention of a user in the system, for example for pipetting liquids, is required so that the system remains closed during the method. In this way, particularly high sterility can be ensured. In addition, a continuous process can be ensured in this way, which enables uniform growth of the cells.

Thus, the method may comprise carrying out a multi-step cell culture process automatically over a plurality of culturing steps.

In particular, the method may be carried out entirely with a system arranged in a housing, for example with a table-top device.

The active elements may be pumps and/or valves, for example. The method steps may be carried out particularly by actuating the active components. The actuation may comprise for example opening valves, closing valves, switching a multiway valve, switching on pumps, switching off pumps and/or setting operating parameters of pumps. Switching a multiway valve enables changing a transport path of liquid in the multiway valve. For example, switching allows liquid to be selectively introduced into different elements connected to the valve such as conduits.

In particular, the valves may each be configured in such a way that they allow neither gas nor liquid to pass through when closed.

Controlling active elements may be carried out by means of a control means that drives the active elements. This indicates particularly that the control means controls the actuation of the active elements.

Various aspects may be adjusted by actuating the active components particularly automatically by controlling the active components. In particular, adjustment may be carried out by establishing and/or interrupting connections between a liquid container in which liquid is stored and the fluid channel system, for example by particularly automatically opening and/or closing valves and/or particularly automatically switching multiway valves and/or applying a pressure suitable for transporting the respective liquid into the fluid channel system, for example by particularly automatically actuating pumps. Thereby the following aspects can be adjusted.

By actuating the active components it is possible to set which liquid is supplied to the fluid channel system. For example, by adjusting valves and/or actuating pumps, liquid can be supplied from a selected storage container with the liquid to be supplied.

Alternatively or additionally, by actuating the active components a sequence of liquids to be supplied to the fluid channel system may be set. For example, by adjusting valves and/or actuating pumps a first liquid can be supplied from a selected storage container with the first liquid to be supplied, and subsequently by actuating (opening, closing and/or switching) valves and/or actuating pumps a second liquid can be supplied from a selected storage container with the second liquid to be supplied.

Alternatively or additionally, it can be set by actuating the active components through which access liquid is supplied to the fluid channel system. This can be carried out for example by actuating valves associated with the accesses.

Alternatively or additionally, it can be set by actuating the active components through which access liquid is removed from the fluid channel system. This can be carried out for example by actuating valves associated with the accesses.

Alternatively or additionally, the transport path of liquid in the fluid channel system may be adjusted by actuating the active components. The transport path may be set by actuating pumps and valves. The transport path may be determined for example, by where the pump applies pressure and how the valves associated with the accesses are set, and possibly by the geometry of the fluid channel system. The transport path may comprise for example the direction of transport of the liquid, particularly through which channels the liquid is transported and in which direction and in which sequence it moves through the channels.

Alternatively or additionally, the flow velocity of liquid in the fluid channel system may be adjusted by actuating the active components. This can be carried out, for example by setting the pressure applied by the pumps. In particular, the flow velocity can also depend on the properties of the liquid, for example viscosity and/or the geometry of the fluid channel system and/or surface properties of the fluid channel system. In particular, the flow velocity can be set such in the substrate, especially in the entire system, that a laminar flow exists. This allows better control of cell transport and preserves the cells.

Alternatively or additionally, it may be set by actuating the active components when liquid is supplied to the fluid channel system and/or is transported further in the fluid channel system and/or is discharged from the fluid channel system. Setting can be achieved by actuating the components at appropriate points in time.

In particular, the active components may be actuated automatically at the corresponding points in time by controlling the active components. The point in time the liquid is supplied and/or transported further and/or discharged, can be decisive for when a particular method step is initiated or terminated. For example, the beginning and ending of growing and thus the amount of cells cultured, depend on when the cells enter and are removed from the culturing channel. The effectiveness of an enzymatic detachment process of cells of the cell culture in the culturing channel depends on how long a detachment liquid remains in the culturing channel.

The movement of the liquids and cells in the substrate may only be set by pressure differences in the closed system with correspondingly opened or closed accesses. By setting the pressure values, the flow velocities can be set.

The method may be carried out automatically by carrying out all method steps in which liquids are moved in the fluid channel system by appropriately controlling active components located outside the substrate.

The method allows to adjust that the cells can multiply over a suitable period of time, wherein, if necessary, the liquid in the culturing channel is replaced, the multiplication is interrupted at a suitable point in time and the cells are then transported away.

If necessary, measuring means and a closed control loop may also be used to individually adjust the method steps for each case. Therefore, it is obvious that no manual steps are required per se to carry out the entire culturing process. Therefore, the culturing process can be carried out fully automated. Alternatively, only parts of the culturing process may be carried out automatically.

In the case of automatically carrying out the method, the time sequence of actuating active components and/or the values of parameters to be set at specific points in time on the active components may be determined in advance, in whole or in part. In particular, said parameters can be determined based on the liquid, flow direction or transport path and/or flow velocity of the liquid in the substrate, required for each of the method steps. For example, the parameters to be set may be the power or the applied pressure of pumps and/or the position of the valves. Alternatively or additionally, at least part of the temporal sequence of the actuation of active components and/or the settings of the values of parameters to be set at the active components may be controlled not in advance but based on target values and measured actual values of process measurands, for example flow velocity, flow rate, temperature, humidity and/or composition of the air. In particular, the actual values of the measurands may be detected during the method by means of measuring means, for example flow sensors, thermometers, hygrometers or detectors for measuring the oxygen content and/or $CO_2$ content in the air. The regulation may be carried out by controlling the components in such a way that the actual values approach the target values. In particular, as part of the regulation, the method may comprise bringing liquids to a predetermined temperature before supplying them into the substrate, particularly into the culturing channel. In particular, this can be carried out actively by means of a heat exchanger, for example.

Regulating the method using the values allows for stabilizing the method and ensuring consistent quality.

The method may comprise that process parameters are measured by means of measuring means, particularly during the entire process. This enables reliable in-process control. In particular, the method may comprise that process parameters such as temperature, humidity, oxygen content and/or $CO_2$ content are measured in the system, especially in to the direct environment of the substrate. If the substrate and/or the system are arranged in a housing, the process parameters can be measured at one or a plurality of locations in the housing, for example.

The method may further comprise that the measured values are stored and/or used to control method steps and/or used to monitor the method. The latter may comprise for example automatically issuing a warning if there are deviations from predetermined values. In particular, the method may comprise access to a reference database with cell-specific data. The cell-specific data and data measured by the method may be used to detect changes in the physiology of the cells. The method may comprise using the measured values to optimize the process parameters, particularly by means of a self-learning system.

In particular, the method may be automated in such a way that the initiation of subsequent method steps is activated automatically on the basis of measured values. For example, an automatic confluence determination may be used to automatically decide when the next cell detachment takes place.

The substrate may be configured in such a way that no active components, particularly pumps and valves, and/or no measuring means and/or no control means are arranged therein. That is, the substrate may be configured in such a way that no valves and/or pumps are arranged between the culturing channel and the storage channel. In particular, all active components, all control means and all measuring means may be arranged outside the substrate. It may therefore be a purely passive substrate. This does not exclude passive elements such as membranes or passive filters from being located within the substrate. For example, semi-permeable membranes may be arranged at one or a plurality of the accesses. In particular, semi-permeable membranes may be configured and arranged such that when liquid is transported out of the substrate the cells remain in the substrate, regardless of the transport velocity of the liquid. In particular, such membranes may be arranged at accesses of channels provided for homogenization and/or concentration, for example at the storage access.

A passive substrate in which only channels and possibly membranes are arranged is advantageous since it can be manufactured as a low-cost disposable product or consumable, and a risk of contamination is reduced.

The cells of the cell culture may be detached from the walls of the culturing channel enzymatically and/or by means of shear forces generated during movement of a liquid in the culturing channel before they are transferred via the transfer channel into the storage channel. In particular, this step can be carried out when the cells adhere to, especially grow on, the walls of the culturing channel during cell culture growth. For enzymatic detachment, an enzyme-containing liquid, for example trypsin, may be transported into the culturing channel. The method may comprise that the enzyme-containing liquid remains in the first culturing channel for a predetermined period of time and then is transported away. The cells may be transferred in whole or in part with the enzyme-containing liquid or may be transferred using a separate transfer liquid. If the cells are detached from the walls by shear forces, this can be achieved by suitable direction and flow velocity of the liquid. In particular, bidirectional flow can also be used to detach cells by shear forces.

The method may comprise optical inspection of the cells during growing and/or during detachment and/or while the cells are located in the storage channel. In particular, the inspection may comprise determining cell density or cell number, especially confluence, i.e. cell number per area.

The determination of the cell number per area may be carried out in the culturing channel, for example during the detachment process or afterwards. Alternatively or additionally, the determination of the cell number may be carried out in the storage channel before the cells are transferred to another culturing channel. In particular, the cells can only be transferred to an additional culturing channel if the inspection shows that a suitable cell density or cell number is present. Seeding in an additional culturing channel with a suitable cell density or cell number enables particularly uniform growth behavior.

Analyzing the cell morphology may be carried out using the optically taken images of the cell culture. In particular, AI (artificial intelligence) algorithms can be used for this. Currently deep learning algorithms are best suited for this, such as those provided free of charge by Google's TensorFlow module. The morphology of the cells can be used to evaluate the state of the cells and automatically adjust the cell culture parameters to improve the cell culture.

The optical inspection may comprise that, based on a microscopically imaged area of the growth area, the confluence representative of the entire growth area is determined. The optical inspection may optionally comprise examining a plurality of areas of the substrate. For this purpose, particularly a lens of an optical measuring means and/or the substrate can be moved particularly automatically. By examining a plurality of areas, particularly a representative inspection of the entire population and its quality can be carried out. Optionally, the optical inspection may comprise a contrast enhancing method, for example using phase contrast, dark field illumination, Digital Holographic Microscopy (DHM) or Differential Interference Contrast (DIC). Optionally, fluorescence-based techniques such as wide-field fluorescence or confocal fluorescence-scanning microscopy may also be used. Optical inspection may comprise that cells are counted automatically.

The culturing channel may be a first culturing channel and the transfer liquid may be a first transfer liquid. The fluid channel system may then comprise at least one second culturing channel fluidically connected to the transfer channel. The second culturing channel and any additional culturing channels may each have one or a plurality of the features described with reference to the (first) culturing channel. The culturing channels may all open into the transfer channel or may be otherwise fluidically connected thereto. In particular, a plurality of culturing channels may be arranged along the transfer channel, particularly parallel to each other, particularly adjacent to each other.

The method may comprise transferring, particularly after storage and/or concentration and/or homogenization and/or dilution, the cells from the storage channel via the transfer channel into the second culturing channel by means of a second transfer liquid and growing an additional cell culture by multiplying the cells in the second culturing channel. The second culturing channel may have its own or separate culturing access.

In particular, the transfer channel may be fluidically connected to all culturing channels, and each transfer step of cells may be carried out via the transfer channel. Thus, it represents a central connecting structure in the substrate.

The transfer channel enables separate control of the individual channels connected thereto, for example the culturing channels and the storage channel or channels, respectively. In addition, the transfer channel and the access of the storage channel or the culturing channel can be used to transport liquid through the storage channel or culturing channel without having to transport the liquid through other channels. Thus, the other channels do not come into contact with the liquid to be transported, which reduces contamination risks, and optionally the other channels can be used for other purposes at the same time since they remain unaffected by the transport of the liquid.

The first and second transfer liquid may have the same or a different material composition. In particular, they may have the same material composition and may be supplied from the same liquid container.

The transfer channel may optionally also be used for processing, particularly for diluting cell suspension in the substrate.

In addition to the storage channel, the fluid channel system may also have other storage channels, each of which may have one or a plurality of the properties described in conjunction with the storage channel. The storage channels may all open into the transfer channel or be otherwise fluidically connected thereto. By way of example, an equal number of storage channels and culturing channels may be formed in the substrate.

After growing the second cell culture, transferring cells of the second cell culture from the second culturing channel to the storage channel or to another storage channel via the transfer channel may optionally be carried out. The second culturing channel may have a culturing access, and the transfer may be carried out by supplying a third transfer liquid through the culturing access of the second culturing channel and transport of the third transfer liquid may be carried out through the second culturing channel and the transfer channel into the storage channel.

The steps described above may be repeated, that is, successive additional cell cultures can be grown each in an additional culturing channel with the cells in between being transferred to the storage channel or additional storage channels.

The method may comprise that cells are removed from the storage channel, particularly directly through the storage access or indirectly via the transfer channel through the transfer access and/or that cells are removed from the culturing channel, particularly directly through the culturing access or indirectly via the transfer channel through the transfer access. For example, the removal may be carried out at the end of the method. Alternatively, the removal can also represent an intermediate step in the method. For example, this allows excess cells to be removed, cells to be removed for testing, or the final processed cells to be removed.

The method may comprise, as described above by way of example for the first culturing channel, supplying nutrient liquid into the fluid channel in which cells are located, and/or discharging nutrient liquid from the fluid channel, particularly from the fluid channel system. In particular, these steps may be carried out repeatedly. In other words, the method may comprise replacement of the nutrient liquid in the respective fluid channel.

The method may comprise a step of flushing at least part of the fluid channel system and/or fluidic components and/or active components and/or liquid containers of the system. In particular, a flushing step may be carried out between each two culturing steps, particularly a flushing step of the components located outside the substrate. The flushing step may be carried out automatically.

The invention also refers to a substrate for culturing cells, particularly for culturing cells by means of one of the methods described above. In the substrate, a fluid channel system is formed, comprising a culturing channel for growing a cell culture having a culturing access to the outside, a storage channel for storing and/or concentrating and/or homogenizing and/or diluting a cell suspension containing the transferred cells having a storage access to the outside, and a transfer channel having a transfer access to the outside. The culturing channel and the storage channel are fluidically connected to each other via the transfer channel.

Features and advantages described above in conjunction with the process, particularly with respect to the substrate used in the process, apply analogously to the substrate.

The substrate may comprise a bottom plate and a top plate, the top plate having recesses defining the channel structures of the substrate and being connected to the bottom plate in a fluid-tight manner.

The bottom and top plate may each be two injection molded parts, one deep drawn and one flat sheet or one injection molded part and one flat or deep drawn sheet. The bottom plate may have a thickness between 0.2 μm and 2 mm. The substrate may comprise the top plate and the bottom plate and top plate may have the same width and length. The bottom plate and top plate may be irreversibly connected to each other, particularly glued, ultrasonically bonded, or bonded via heat or a solvent.

The substrate may be made of a plastic, particularly a biocompatible plastic. The plastic material may comprise for example polycarbonate, polystyrene, polyethylene, polyvinyl chloride, cyclo-olefin copolymer, cyclo-olefin polymer or polymethyl methacrylate.

The substrate, particularly the bottom plate and/or the top plate, may be made of material that is configured in such a way that microscopic inspection of cell growth is possible. In particular, the birefringence of the material may be low enough to allow microscopic inspection, and/or the fluorescence of the material may be low enough to allow inspection with fluorescence microscopy. In particular, the refractive index of the material may be between 1.2 and 1.6.

The substrate, particularly the floor plate, may consist of a gas-permeable material. This ensures an optimal supply of gases to the cells.

The substrate may be configured in such a way that no active components, particularly no valves and no pumps, are arranged between the culturing channel and the transfer channel and between the transfer channel and the storage channel.

In particular, the substrate may be configured in such a way that no active components, particularly no pumps and no valves, no measuring means and no control means are arranged in the substrate. The substrate may be a purely passive substrate, as explained in detail above.

The fluid channel system may be configured, particularly may have such a shape, arrangement, orientation and/or connection of the channels, particularly the culturing channel, the transfer channel and the storage channel, and the accesses, that only by selectively opening and closing the accesses and/or applying pressure to the fluid channel system, liquids are moved through the fluid channel system along the transport paths designated for the respective method step, and/or are moved through the fluid channel system at flow velocities required for the method step.

The culturing channel, the storage channel and the transfer channel may be arranged in the substrate in one plane. In the case of a substrate with a height that is less than the length and the width, the channels may particularly all be arranged in one level.

The diameter of the transfer channel may be smaller than or equal to the diameter of the culturing channel and/or the storage channel. The maximum diameter of the respective channel is decisive.

A mouth of the culturing channel into the transfer channel may be offset along the transfer channel from a mouth of the storage channel into the transfer channel.

The longitudinal axis of the transfer channel may be arranged at an angle greater than or equal to 50°, particularly greater than or equal to 55°, particularly greater than or equal to 65°, particularly greater than or equal to 75°, particularly greater than or equal to 85°, particularly substantially perpendicular to the respective longitudinal axis of the culturing channel(s).

Alternatively or additionally, the longitudinal axis of the transfer channel may be arranged at an angle smaller than or equal to 40°, particularly smaller than or equal to 35°, particularly smaller than or equal to 25°, particularly smaller than or equal to 51°, particularly smaller than or equal to 5°, or substantially parallel to the longitudinal axis of the storage channel. The transfer channel and the storage channel may be connected, particularly in this case, by a fluid connection having a diameter smaller than or equal to the diameter of the transfer channel and/or the storage channel. In particular, the fluid connection may be substantially perpendicular to the transfer channel.

Alternatively or additionally, the longitudinal axis of the transfer channel may be arranged at an angle greater than or equal to 50°, particularly greater than or equal to 55°, particularly greater than or equal to 65°, particularly greater than or equal to 75°, particularly greater than or equal to 85°, particularly substantially perpendicular to the longitudinal axis of the storage channel.

The culturing channel may be narrowed towards the transfer channel, the narrowest point having particularly a diameter smaller than or equal to half, particularly smaller than or equal to one third, particularly smaller than or equal to one quarter of the maximum diameter of the culturing channel.

Alternatively or additionally, the storage channel may be narrowed towards the transfer channel, the narrowest point having particularly a diameter that is smaller than or equal to half, particularly smaller than or equal to one third, particularly smaller than or equal to one quarter of the maximum diameter of the storage channel. This narrowing is particularly advantageous when the longitudinal axis of the transfer channel is at an angle greater than or equal to 50°, particularly substantially perpendicular to the longitudinal axis of the storage channel, because then the narrowing makes it possible to delimit the areas.

At least one wall of the culturing channel, particularly the floor, may have a surface property of the material, particularly a material property and/or a structural property, and/or a coating that promotes the growing-on of cells, particularly a hydrophilic coating and/or a cell-adherent coating.

Alternatively or additionally, at least one wall, particularly all walls of the transfer channel and/or the storage channel may have a surface property of the material, particularly a material property and/or a structural property, and/or a coating that avoids cell adhesion and/or growing-on of cells, particularly a hydrophobic coating and/or a cell-repellent coating. A hydrophobic coating in the transfer channel and/or storage channel can also prevent deposits from forming there.

Alternatively or additionally, at least one wall of the culturing channel, particularly at least a partial area of the floor or the ceiling or the side walls, may be provided with a surface modification that can be switched with respect to its physical and/or chemical properties in such a way that the switching causes the cells to detach from the surface, particularly with at least one thermoresponsive surface modification, particularly with a coating with poly-N-iso-propylacrylamide (PNIPAM)-based polymers. In this case, cooling the ambient temperature to less than 32° C. changes the surface properties so that proteins anchored to it and thus cells adhering to it detach from the surface. This can be used to allow cells to be detached from the surface with less or even no trypsin or equivalent substances.

Alternatively or additionally, at least one wall of the culturing channel, particularly at least one partial area of the floor, may be provided with a regenerable surface modification which, particularly is configured in such a way that the cell adhesion can be changed and/or activated and/or deactivated.

For surfaces with a regenerable surface modification cell adhesion may be achieved, for example via competitive inhibition (for example, by means of host/guest systems such as dendrimer/peptides, avidin/biotin or adamantane/cyclodextrin), via photoswitchable binding motifs/peptides (such as nitrophenyl-modified binding motifs), via enzymatic digestion of an extracellular matrix (e.g. collagenases or other proteases), via pH-change or change of chemical potential (pH- or redox-switchable block polymers such as poly (2-(diisopropylamino)ethyl methacrylate/poly (2-(methacryloyloxy)ethyl phosphorylcholine block polymer) and/or via chelating agents such as EGTA/EDTA or His-Tag.

The advantage of such regenerable surface modifications is that the growth area of the culturing chambers can be used repeatedly for growing cell cultures, especially for successive cell cultures. In addition, the space required for growing a plurality of cell cultures is reduced, since a separate culturing channel does not have to be provided for each cell culture.

At least one wall of the culturing channel, particularly at least one partial area of the floor and/or of the side walls, may have a structuring which is configured in such a way that the growth surface, particularly the surface covered and/or flushed with liquid, such as cell suspension during intended use, is increased. In particular, it may have a saw tooth profile and/or a corrugated profile and/or a lamellar structure and/or fibrous and/or porous or spongy areas. The floor of the storage channel may have a structuring, for example a saw tooth profile and/or a wave profile, which is configured in such a way that the movement of cells lying on the floor is made more difficult, particularly prevented, in at least one direction. This particularly enables concentrating of the cells.

The arrangement of hydrophilic coating in the culturing channel and hydrophobic coating in the transfer channel supports, in addition to the geometric configuration of the channels, the boundaries between the channels. The invention also refers to a system comprising any of the substrates described above for culturing cells. Features and advantages described above in conjunction with the method and the substrate apply analogously to the system.

A system, comprising one of the substrates described above and at least three liquid containers, such as process liquid storage containers and/or waste containers, arranged outside the substrate. The culturing access, the storage access and the transfer access are each fluidically connected to at least one of the liquid containers. The system also comprises particularly controllable, active components, particularly pumps and/or valves, which are configured and arranged in such a way that, when actuated, particularly controlled, they cause a controlled supply of liquids from the liquid containers into the fluid channel system and/or a controlled transport of the liquids in the fluid channel system and/or a controlled discharge of liquids from the fluid channel system, particularly into the waste container.

All active components of the system may be located outside the substrate.

Used as intended, the substrate may be arranged horizontally, wherein particularly the longitudinal axes of all channels may be arranged horizontally. In particular, all channels can be arranged in one plane.

In particular, the system may comprise all active components used to carry out the method automatically.

The system may comprise a housing in which the substrate, active components, liquid containers and at least some of the measurement means are arranged. The interior of the housing may provide one or a plurality of process rooms and one or a plurality of storage rooms, each of which may be air conditioned particularly independently from one another. The substrate may be arranged in the process room. Storage containers for process liquids may be arranged in the storage room. The fact that the rooms are air-conditioned may comprise that the temperature in the respective process room or storage room is set particularly also time-dependent and is particularly automatically controlled. In addition, the oxygen content and/or the $CO_2$ content and/or the humidity can be set particularly automatically controlled. In order to control the respective parameters, the system may comprise sensors in the respective process room or storage room that measure the temperature, oxygen content, $CO_2$ content and/or air humidity.

The system may comprise fluid connections such as Luer connections through which the channels of the substrate are fluidically connected to liquid containers. The connections may be attached to or be integrally formed with the substrate.

In particular, the connections may be configured for sterile connection. This also applies to connections on the liquid containers. Known sterile connections can be used for this purpose. In this way, a sterile closed fluid system can be provided and thus good quality of the cultured cells can be ensured.

The at least three liquid containers may comprise at least two storage containers for process liquids, such as for an initial cell suspension and for a transfer liquid, and a waste container.

The system may also comprise a plurality of identical or different substrates. This allows high flexibility in terms of throughput and cell lines that can be cultured in parallel.

The system may comprise a plurality of conduits, for example in the form of hoses, by which the substrate is connected to the liquid containers. Each of the accesses may be connected to at least one of the conduits.

The culturing access may be connected to a valve that is configured to establish fluid connection between the culturing channel and at least one of the storage containers, and to establish fluid connection between the culturing channel and the waste container. Alternatively, the culturing access may be connected to two valves, one of which is adapted to establish a fluid connection between the culturing channel and at least one of the storage containers and the other one of which is adapted to establish a fluid connection between the culturing channel and the waste container.

Alternatively or additionally, the storage access may be connected to a valve adapted to establish a fluid connection between the storage channel and the waste container, and particularly to establish a fluid connection between the storage channel and at least one of the storage containers.

Alternatively or additionally, the transfer access may be connected to a valve configured to establish a fluid connection between the transfer channel and at least one of the storage containers and to establish a fluid connection between the transfer channel and the waste container. In particular, the valve may additionally be configured to establish a fluid connection between the transfer channel and at least one of the storage containers. Alternatively, the transfer access may be connected to an additional valve, wherein the additional valve is configured to establish a fluid connection between the transfer channel and at least one of the storage containers.

A connection between an access and a valve means a connection which is not implemented via other channels of the fluid channel system, in this case referred to as directed connection. A connection associated with the respective access, for example a Luer connection, may be provided for this purpose.

In particular, the connection may be established in each case by a multiway valve or by a check valve, particularly by at least two check valves connected in parallel.

Establishing a fluid connection to one of the process liquid storage containers may comprise establishing a fluid connection to a conduit connected to the storage containers, wherein each of the storage containers is connected to the conduit particularly via a check valve.

The system may comprise at least one measuring means arranged outside the substrate, which is configured to measure process measurands, particularly flow velocity and/or flow rate and/or temperature, and/or one measuring means arranged outside the substrate, which is configured to optically inspect the cells in the substrate. All measuring means can be arranged outside the substrate as explained in detail above.

In addition to the measuring means, the system may also comprise a storage means which is configured to receive and store data from the measuring means. The data can be used for example for documentation and analysis of the culturing process.

The system may alternatively or additionally comprise a control means which is configured to control the active components in such a way that one of the methods described above is carried out particularly automatically. The control means can be adapted to carry out the control and/or regulating steps described in the method.

The control means may be connected via a data link to the at least one measuring means for measuring process measurands and/or to the measuring means for optical inspection of the cells.

In particular, the control means may be adapted to regulate values of parameters to be set on the active components, based on target values and measured actual values of process measurands which are detected by means of the measuring means for measuring process measurands.

The invention also refers to the use of any of the substrates or systems described above for carrying out any of the methods described above.

Further features and advantages are explained below with reference to the exemplary drawings, wherein FIG. 1 shows a schematic not to scale top view of a substrate of a first embodiment;

In the following and in the Figures the same reference numerals are used for the same or corresponding elements in the various embodiments unless otherwise specified.

Figure 1:
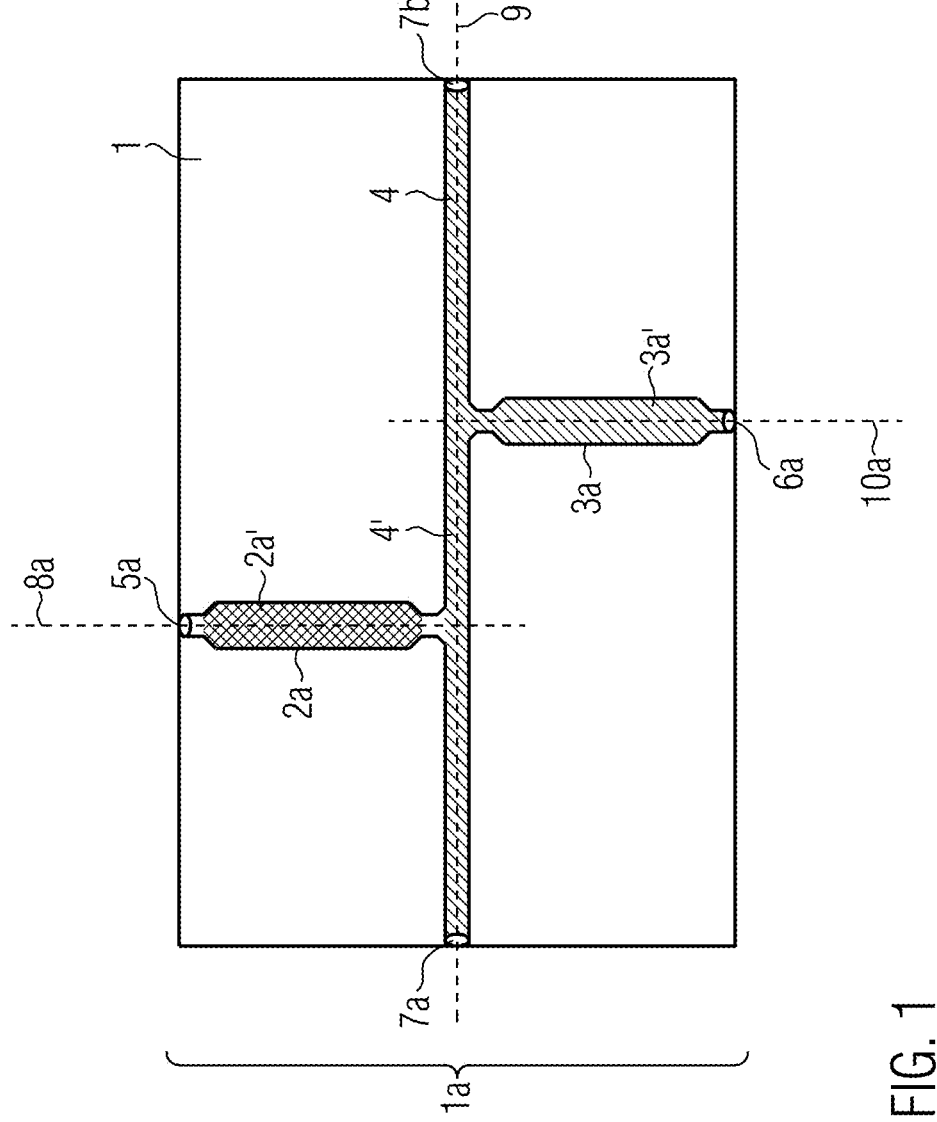

FIGS. 1 to 4 show first to fourth embodiments of a substrate 1 according to the invention. In each of the embodiments shown herein a fluid channel system 1a is formed in the substrate 1, comprising a first culturing channel 2a, a storage channel 3a, and a transfer channel 4. The first culturing channel has a culturing access 5a. The storage channel has a storage access 6a and the transfer channel has a transfer access 7a. The transfer channel may further optionally have a second transfer access 7b.

In FIG. 1 it is exemplarily indicated that the first culturing channel may comprise a coating 2a'. In particular, this can be a cell-adherent coating or a hydrophilic coating. Furthermore, it is exemplarily indicated that the transfer channel and the storage channel comprise a coating 4' and 3a', respectively. Each of the coatings may be a cell-repellent coating or a hydrophobic coating. The coatings are not shown in FIGS. 2 to 4 but may also be provided in the corresponding embodiments.

Figure 2:
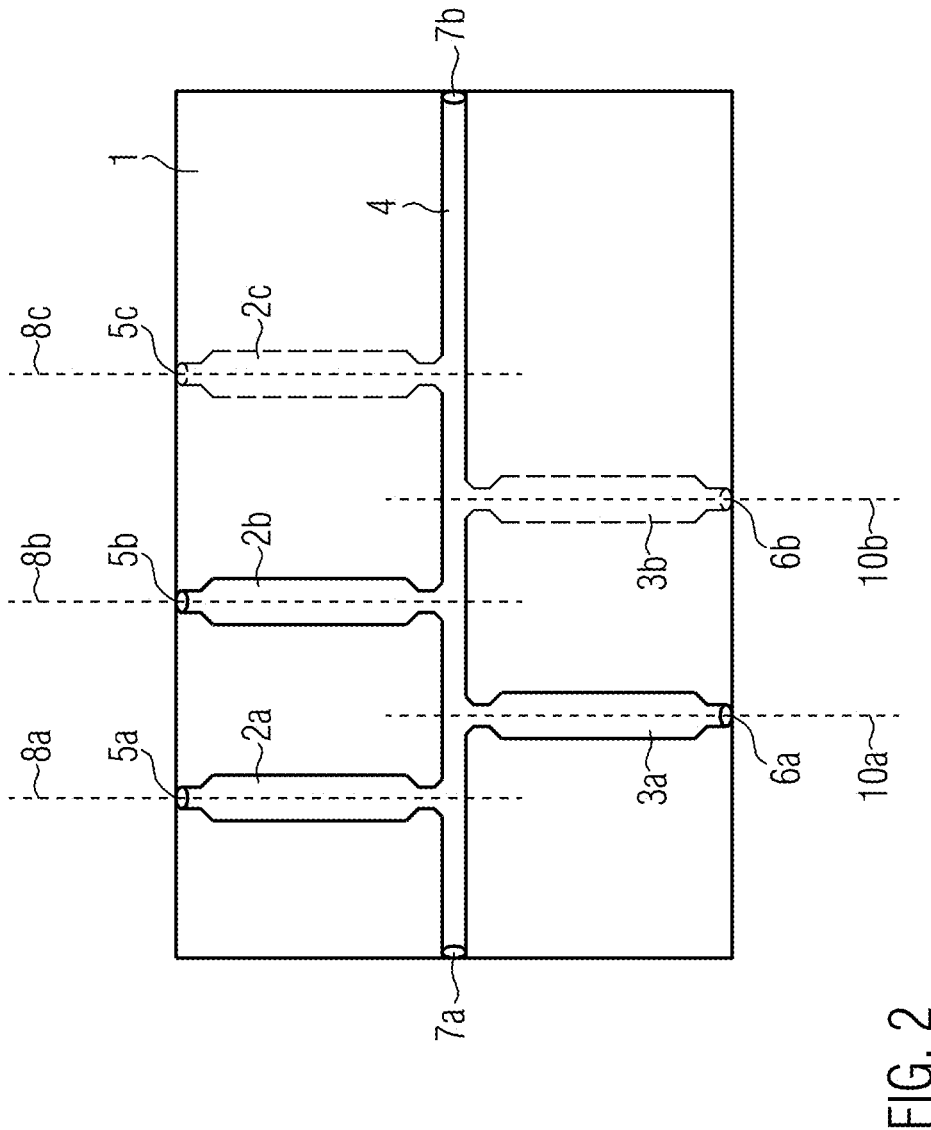
FIG. 2 shows a schematic not to scale top view of a substrate of a second embodiment.
Figure 3:
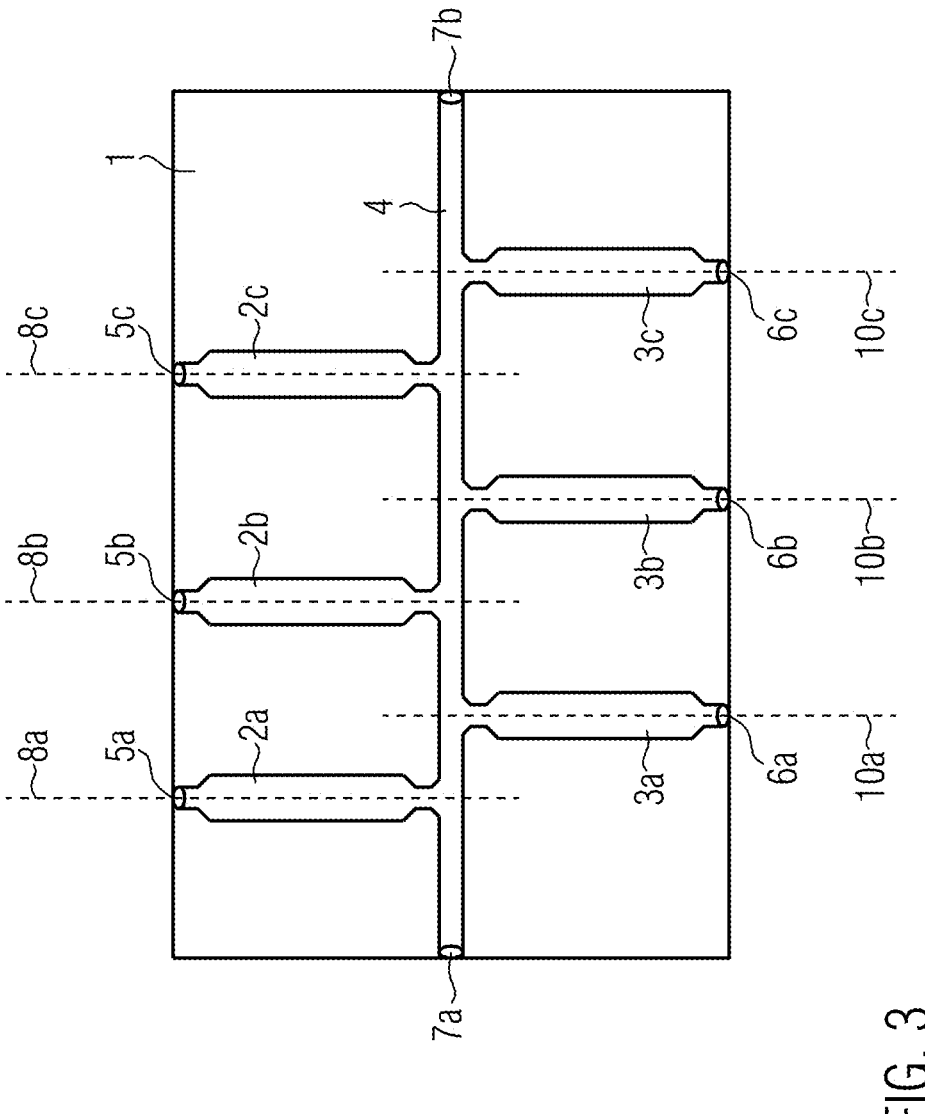
FIG. 3 shows a schematic not to scale top view of a substrate of a third embodiment.
Figure 4:
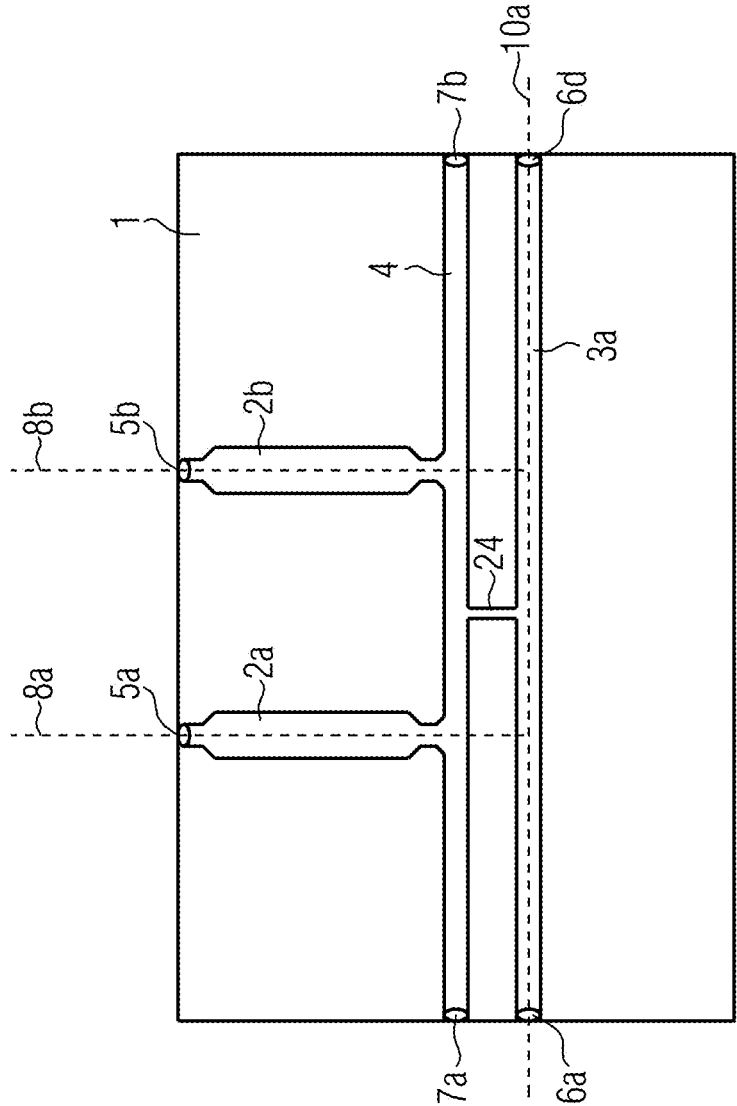
FIG. 4 shows a schematic not to scale top view of a substrate of a fourth embodiment.

In the embodiments shown in FIGS. 2 to 4, the fluid channel system further comprises one or a plurality of additional culturing channels, for example a second culturing channel 2b and a third culturing channel 2c and one or a plurality of additional storage channels, for example a second storage channel 3b and a third storage channel 3c.

The additional culturing channel(s) each have their own culturing access 5*b* and 5*c*, respectively. The additional storage channel(s) each have their own storage access 6*b* or 6*c*, respectively.

In FIG. 2, channels 2*b*, 2*c* and 3*b* are shown by dashed lines. This illustrates that any number of additional channels can be provided, wherein particularly the number of storage channels and the number of culturing channels do not have to be identical. In contrast, FIG. 3 shows an embodiment in which the number of storage channels is equal to the number of culturing channels.

As shown in FIGS. 1 to 4, each of the culturing channels is fluidically connected to the transfer channel. In this example, each of the culturing channels is narrowed towards the transfer channel, that is, the diameter of the mouth of the respective channel is smaller than the diameter in other areas of the channel, which, however, is optional. Furthermore, each of the storage channels is fluidically connected to the transfer channel. The longitudinal axes 8*a* to 8*c* of the culturing channels are arranged substantially perpendicular to the longitudinal axis 9 of the transfer channel, which, however, this is not mandatory.

In FIGS. 1 to 3, each of the storage channels is narrowed towards the transfer channel which, however, is optional. Here, in addition, the longitudinal axes 10*a* to 10*c* of the storage channels are arranged along the transfer channel offset from the longitudinal axes 8*a* to 8*c* of the culturing channels, here exemplarily also substantially perpendicular to the longitudinal axis of the transfer channel.

In FIG. 4 the longitudinal axis 10*a* of the storage channel 3*a* is substantially parallel to the longitudinal axis of the transfer channel. The substrate comprises a fluid connection 24 between the storage channel and the transfer channel. The fluid connection has a diameter smaller than the diameter of the storage channel, and its longitudinal axis in this example is arranged substantially perpendicular to the longitudinal axis of the transfer channel and offset from the longitudinal axes of the culturing channels along the transfer channel. The storage channel 3*a* in FIG. 4 may have an additional storage access 6*d* in addition to the storage access 6*a*.

By way of example, in the first to fourth embodiments all channels are arranged in one plane. In particular, when the substrate is used as intended their longitudinal axes are arranged horizontally.

The substrate can be transparent, particularly formed of a transparent plastic material. In particular, the substrate can be configured in such a way that the cells contained therein can be inspected microscopically.

FIGS. 5 to 8 schematically show not to scale fifth to eighth embodiments of a system 11*a* to 11*d* for culturing cells, here exemplarily comprising the substrates shown in FIGS. 1 to 4. However, this is optional and other substrates according to the invention may be used in any of the systems. In particular, the shape, the orientation, the number, the interconnection and/or the coating of the channels in the fluid channel system may be different from those described with reference to FIGS. 1 to 4.

FIGS. 5 to 8 each show by way of example three storage containers for process liquids, for example a first storage container 12*a* for initial cell suspension 12*a'*, a second storage container 12*b* for cell culture medium 12*b'*, and a third storage container 12*c* for a liquid 12*c'* for detaching the cells. It is understood that additional storage containers may be provided for process liquids. Further, as shown in the Figures, the system may optionally comprise a waste container 12*d*. A pump 13*a* to 13*c* may be connected to each of the storage containers 12*a* to 12*c*, respectively. In each case, a filter 14*a* to 14*c*, for example a sterile filter, can optionally be arranged between the pump and the storage container. Depending on the process, a different number of storage containers may also be provided. If necessary, only one pump may also be provided for a plurality of storage containers. The system may then comprise, for example, a valve which is configured in such a way that it can be used to set to which of the storage containers pressure is applied.

At least one valve may be connected to each of the accesses. In the Figures, the culturing access 5*a* is connected to a first valve 15*a*, the storage access 6*a* is connected to a second valve 16*a*, and the transfer access 7*a* is connected to a third valve 17*a*. If provided, the additional culturing accesses 5*b* and 5*c* may each be connected to a fourth valve 15*b* and 15*c*, the additional transfer access 7*b* may be connected to a fifth valve 17*b*, the additional storage accesses 6*b* and 6*c* may each be connected to a sixth valve 16*b* and 16*c* or the port 6*d* may be connected to an additional valve 16*d*.

As shown in FIGS. 5 to 8, the storage containers 12*a*, 12*b* and 12*c* may each be connected to a conduit 19 via a valve 18*a*, 18*b*, 18*c*. The conduit may be connected to the culturing access 5*a* of the first culturing channel via valve 15*a*, to the transfer access 7*a* of the transfer channel via valve 17*a* and optionally to the storage access 6*a* of the storage channel via valve 16*a*. At least one of the remaining accesses 5*b*, 5*c*, 6*b*, 6*c*, 6*d*, and/or 7*b* may also each be connected to the conduit via a valve 15*b*, 15*c*, 16*b*, 16*c*, 16*d*, and 17*b*, respectively. Each of the accesses connected to the conduit can be supplied with one of the liquids in the liquid containers 12 *a* to 12*c* by suitable valve positioning of the valves 18*a* to 18*c* and of the valve associated with the respective access.

Alternatively or additionally to being connected to the conduit, each of the accesses may be connected to the waste container 12*d* via the corresponding valve, optionally via a flow meter 18*d*. The measured values from the flow meter can be used to clearly determine the flow rate in the system if, as shown herein, the system is a closed system. The measure values of the flow meter 18*d* can then be used as a control and/or regulating variable, particularly for actuating the valves.

Figure 8:
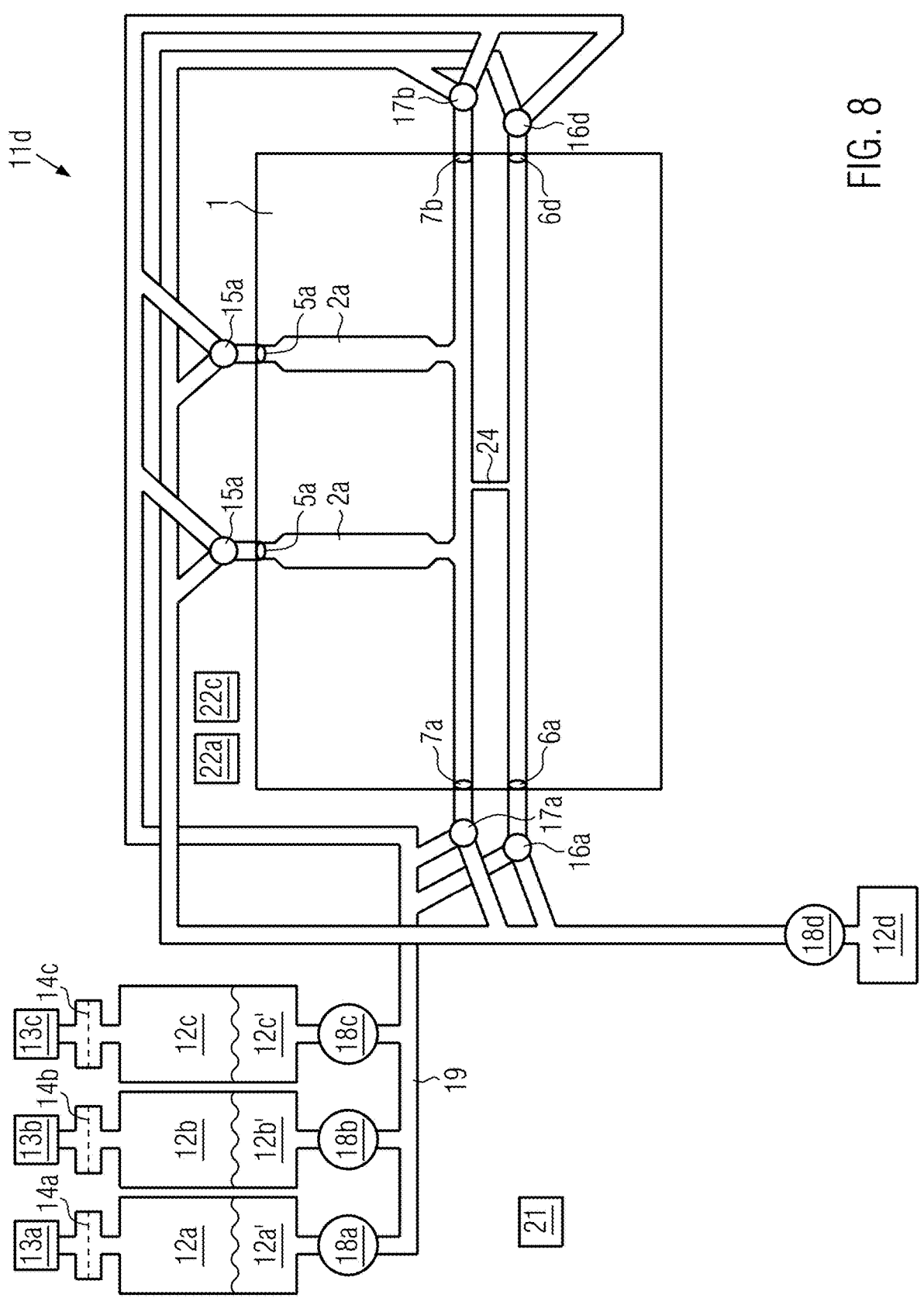
FIG. 8 shows a schematic not to scale representation of a system of a seventh embodiment using a substrate of the fourth embodiment as an example.

In the embodiment shown in FIG. 8, the storage channel 3*a* has two accesses 6*a* and 6*d*. Here, both accesses are connected to the conduit and to the waste container via valves. Alternatively, one of the accesses, for example access 6*a*, may be connected exclusively to the conduit 19 via valve 16*a*, and the other access, for example access 6*d*, may be connected exclusively to the waste container 12*d* via valve 16*d*.

Figure 9:
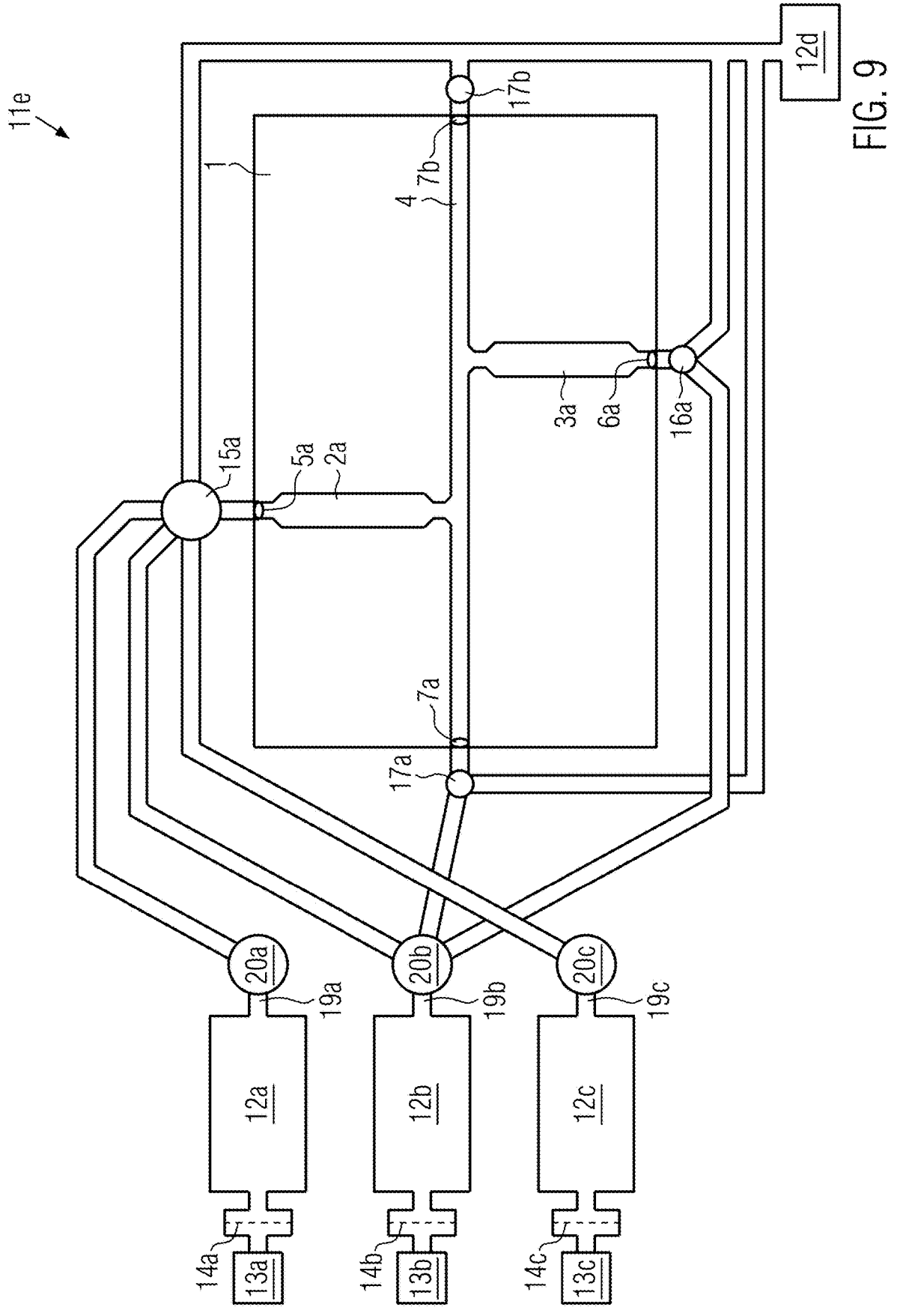
FIG. 9 shows a schematic not to scale representation of a system of an eighth embodiment.

FIG. 9 shows an alternative system 11*e*. The system also comprises four liquid containers 12*a* to 12*d*, for example the storage containers and waste containers described above, three pumps 13*a* to 13*c*, and filters 14*a* to 14*c*. Further, it shows valves 15*a*, 16*a*, 17*a* and 17*b* connected to accesses 5*a*, 6*a*, 7*a*, 7*b*, respectively. As an example, the system is shown with the substrate of the first embodiment, but any substrate according to the invention may be used instead. Here, the three liquid containers are not connected to a common conduit 19. Each of the liquid containers has its own conduit 19*a* to 19*c*, and the liquid can be supplied to each of the accesses via a valve 20*a* to 20*c* through the valve connected to the respective access.

In the embodiment shown here, initial cell suspension from the container 12*a* can be supplied to the first culturing channel 2*a* via the valve 20*a* and the valve 15*a*. Liquid from the container 12*b* can be supplied to the accesses 15*a*, 16*a* or 17a via the multiway valve 20b. Liquid from the container 12c, for example liquid for detaching cells, can be supplied to the first culturing channel via the valve 20c. In addition, liquid from the first culturing channel 2a can be supplied to the waste container 12d through the valve 15a, liquid from the transfer channel 4 can be supplied to the waste container through the valve 17b, and liquid from the storage channel 3a can be supplied to the waste container through the valve 16a.

In each of FIGS. 5 to 9 an optionally provided control means 21 is shown.

Figure 5:
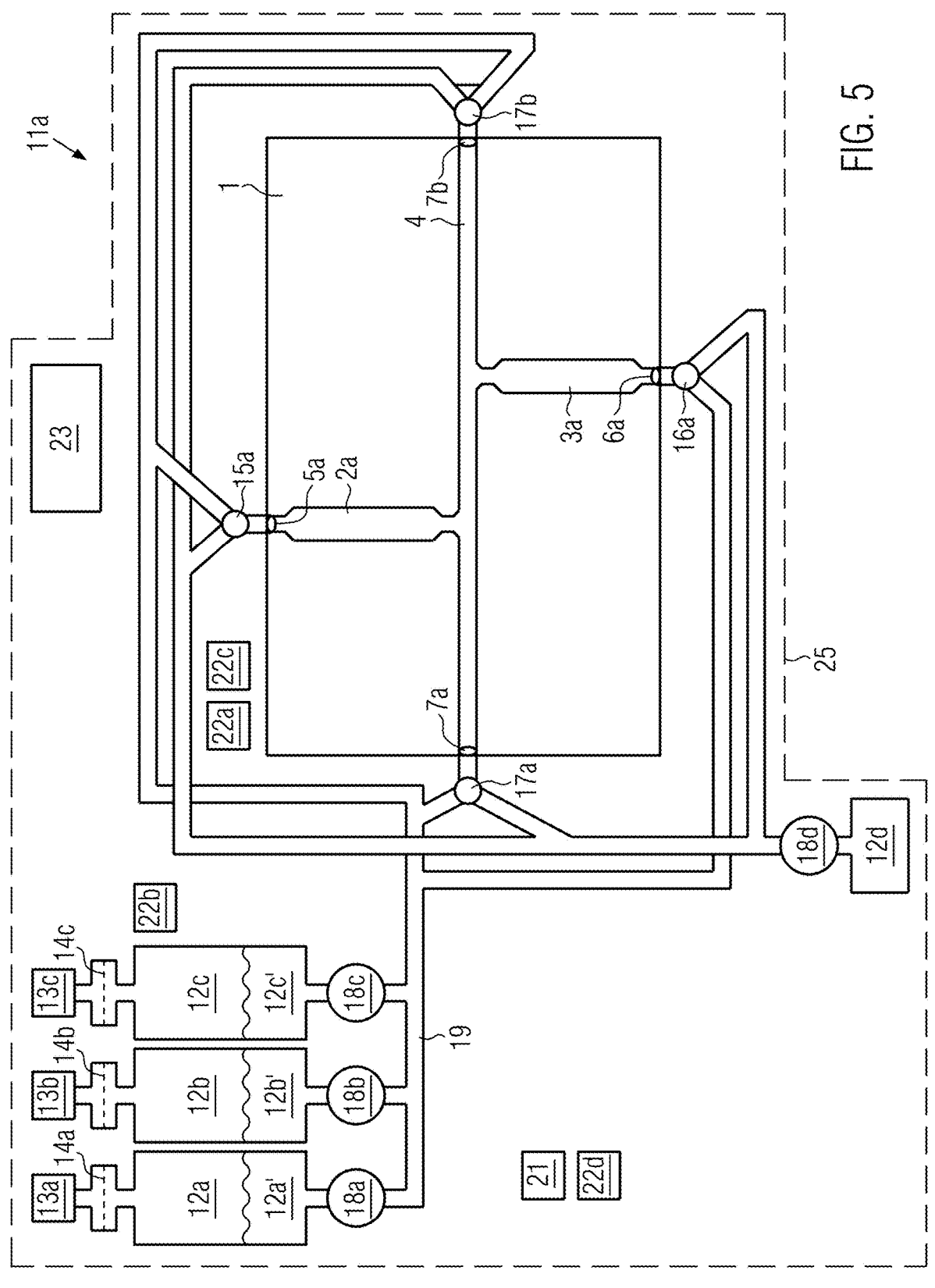
FIG. 5 shows a schematic not to scale representation of a system of a fifth embodiment using the example of a substrate of the first embodiment.

FIG. 5 shows optionally provided sensors 22a to 22d. For example, sensor 22a is configured and arranged to measure the humidity in the area of the substrate. Sensor 22b is configured and arranged to measure the temperature in the area of the liquid container. Sensor 22c is configured and arranged to measure the temperature in the area of the substrate. Sensor 22d may be a sensor for measuring the oxygen or $CO_2$ content of the air in the system. In particular, one or a plurality of the sensors may be arranged within a housing 25 along with the substrate and/or the liquid containers.

Furthermore, an optionally provided means for optical inspection 23 is indicated schematically. This can be a microscopy means. The substrate may be in the form of a microscopy carrier. The means for optical inspection may be arranged at least partially within the housing, which enables monitoring without intervention in the system. Alternatively, the optical inspection means may be arranged outside the housing and the housing may be removable.

The sensors, the optical inspection means and the housing are not shown in FIGS. 6 to 9, but the systems shown there may also comprise one or a plurality of these sensors, an optical inspection means and/or a housing.

Figure 6:
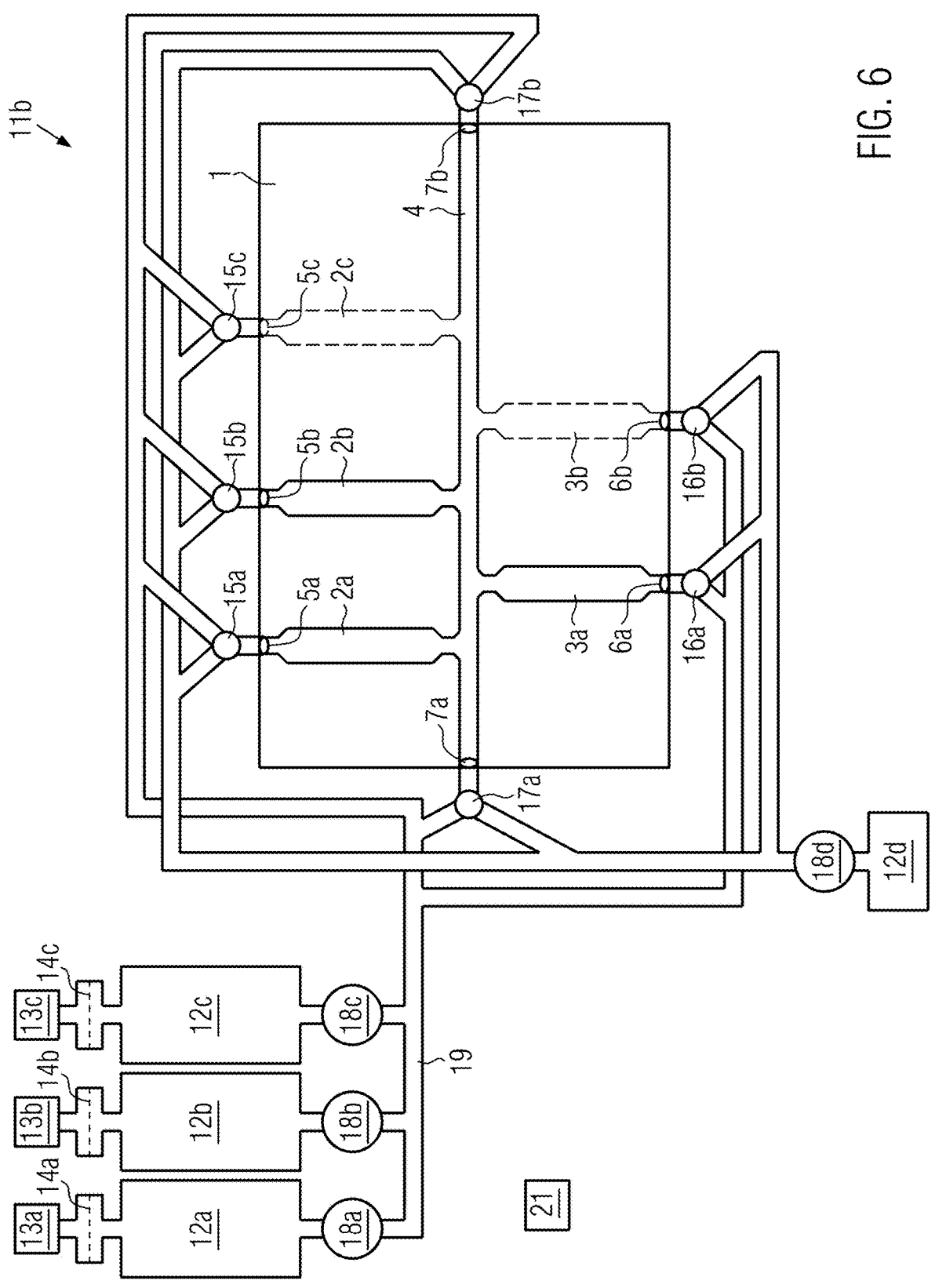
FIG. 6 shows a schematic not to scale representation of a system of a sixth embodiment using the example of a substrate of the second embodiment.

In the following, a method for culturing cells is illustrated, here exemplarily using the system of the sixth embodiment, as shown in FIG. 6. Said method can also be carried out analogously with other systems, particularly those described above. In the following, possible modifications suitable for a differently configured system are illustrated at the appropriate point by way of example.

In this example the liquid container 12a contains an initial cell suspension, a liquid in which the cells to be seeded are suspended. The liquid container 12b contains a cell culture medium. The liquid container 12c contains a liquid for detaching cells, for example trypsin. If such a liquid is not required for the corresponding application, it is understood that this storage container can be renounced.

In the first step liquid is transported from the storage container 12a into the first culturing channel using the pump 13a. For this purpose, the valves 15a, 17a and 18a can be actuated. All other valves are closed in this example. Opening the valve 18a enables initial cell suspension from the storage container 12a to enter the conduit 19.

Depending on whether the valve 15a or 17a is opened to the conduit, the initial cell suspension is transported into the first culturing channel via access 5a or 7a, respectively, provided the other valve is opened to the waste container 12d. The initial cell suspension remains in the culturing channel or flows slowly through the first culturing channel. The cells settle in the first culturing channel and may adhere to the walls of the channel. The liquid of the initial cell suspension can then optionally be transported out of the first culturing channel into the waste container or remain in the culturing channel for the time being.

In the first culturing channel, the cells begin to multiply. Optionally, a nutrient liquid can be transported into the first culturing channel, for example via the same path as the initial cell suspension, and then be discharged from the same when the nutrients have been used up.

In an optional second step, when the cells have multiplied and formed a first cell culture, the liquid for detaching the cells is transported from the storage container 12c to the first culturing chamber using the pump 13c. For this purpose, valves 15a, 17a and 18c are actuated. All other valves are closed in this example. Opening the valve 18c allows the liquid from the storage container 12c to enter the conduit 19. From there, the liquid enters the first culturing chamber in the same way as the initial cell suspension did before. The second step may be renounced if the cells do not or not very strongly grow on the walls of the culturing chamber. In particular, if the growing-on is not strong the detachment may be purely mechanical, for example by shear stress.

In a third step, the cells are transferred from the first culturing channel via the transfer channel into the first storage channel. For this purpose, the valve 18b is opened so that cell culture medium from the liquid container 12b enters the conduit 19. The cell culture medium is introduced into the first culturing channel through the culturing access 5a using the pump 13b and is transported into the storage channel through the transfer channel. In the process the cells are transferred into the storage channel. In this step, the valve 15a is opened to the conduit. Moreover the valve 16a is opened for example towards a waste container.

The method for culturing cells according to the invention may already end after the cells have been transferred to the storage channel. The cells can be temporarily stored and/or inspected in the storage channel.

Optionally, the method may further comprise one or a plurality of the following steps.

For example, in an optional fourth step concentration of the cell suspension can be carried out for example in the storage channel. For this purpose, the property of the cells that they sink to the floor is used. By setting a sufficiently low flow velocity and optionally supported by structuring the floor of the storage channel, the cells remain in the storage channel while part of the cell culture medium is transported further out of the storage channel so that the cell concentration is increased.

Alternatively or additionally, in an optional fifth step the cell suspension in the storage channel can be homogenized for example by mixing it. Optionally, after homogenization an optical inspection of the cells can be carried out, which are now arranged more uniformly in the storage channel. If a homogeneous cell distribution is present due to the homogenization, an optical inspection of the cells at a few positions in the substrate is sufficient to make representative statements about the entire cell culture.

Alternatively or additionally, in an optional sixth step dilution of the cell suspension located in the storage channel or the transfer channel can be carried out. For this purpose, the valve 18c can be opened so that cell culture medium enters the conduit and is transported into the storage channel 3a by means of the pump 13c, particularly through the access 6a via the valve 16a. At the same time another valve for example valve 15a or, if present, valve 15b, 17a or 17b, is opened for example towards the waste container.

If no further culturing of the cells in the substrate has to be carried out following these steps, a substrate without additional culturing channels can be used, for example as shown in FIGS. 1 and 5.

If the method comprises further culturing steps, a seventh step is a transfer of the cells through the transfer channel into the second culturing channel 2b. For this purpose, the valve 18b can be opened so that cell culture medium enters the conduit and is transported into the storage channel 6a by means of the pump 13b, particularly as shown here through the access 6 via the valve 16a. In addition, the valve 15b is opened for example towards the waste container. The cell culture medium is then transported together with the cells from the storage channel via the transfer channel into the second culturing channel. There, the cells can multiply and thus a second cell culture can be grown.

The steps described above can be repeated for additional culturing chambers.

In this case, the cells of each of the cell cultures can each be temporarily stored in the first storage channel or can each be transported to a separate storage channel associated with the respective culturing channel, for example storage channels 3b or 3c, and stored there and optionally further processed and/or inspected.

It is also conceivable that a plurality of culturing channels are provided in a substrate to which initial cell suspension is supplied. In other words, a plurality of first culturing channels may be provided. Thus, a plurality of first cell cultures can already be grown in the first culturing step. In other words, a plurality of first cell cultures can be grown in parallel with each other. Thus, many cells can be grown within a short time. If instead the same number of culturing channels is used sequentially, the method can be automated over a longer period of time without using channels twice.

If additional culturing steps each take place in additional culturing channels, a consistent surface quality can easily be ensured for each of the culturing steps. The method can then be carried out without preparation or cleaning of the first culturing channel. However, a second culturing step in the first culturing channel instead of or in addition to a culturing step in another culturing channel is also conceivable. In this case, a return from the storage channel to the first culturing channel would be carried out through the transfer channel, wherein particularly a cleaning step for cleaning the culturing channel can be carried out between the culturing steps. This is advantageous in that a more compact substrate can be used.

Figure 7:
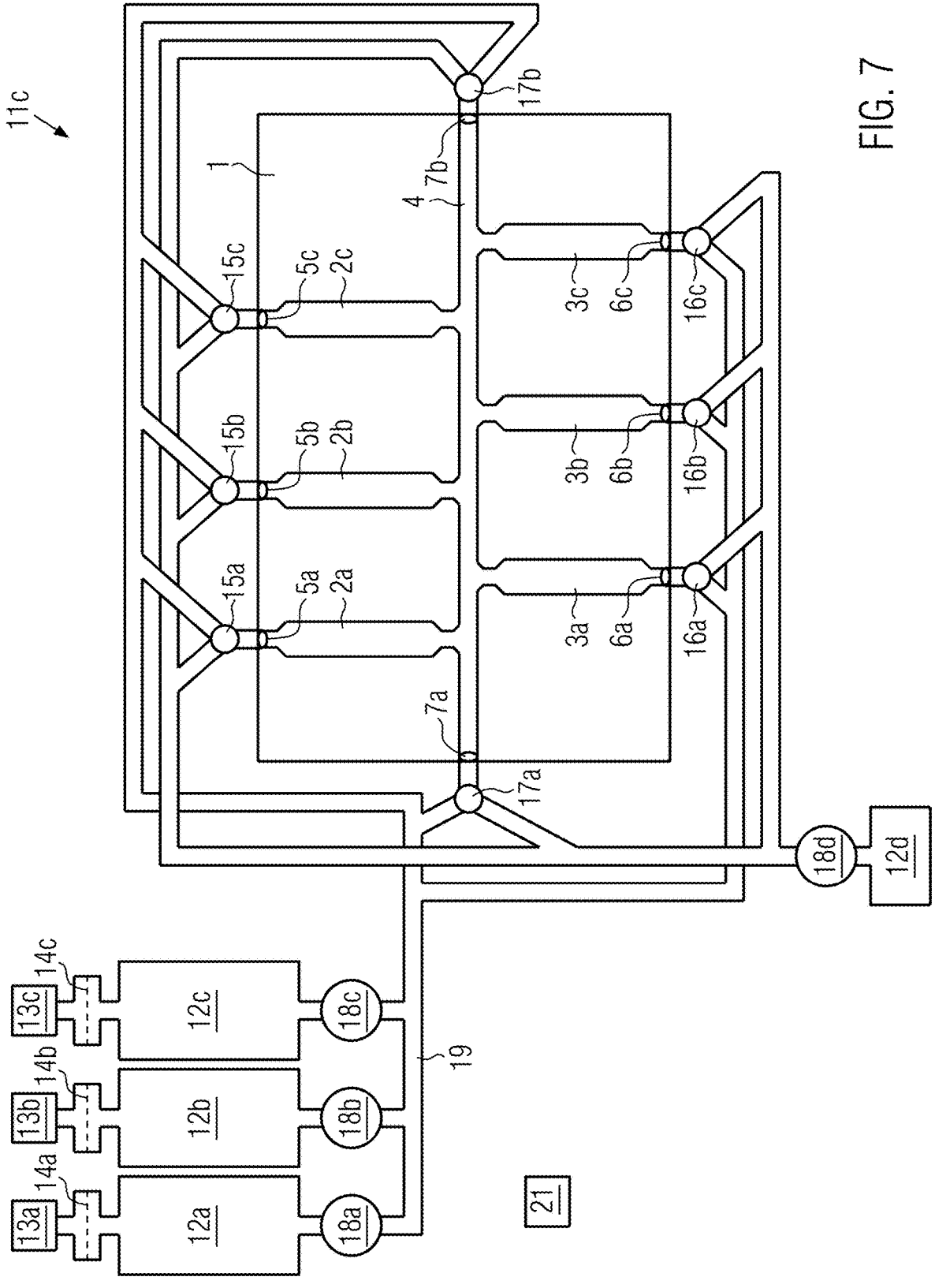
FIG. 7 shows a schematic not to scale representation of a system of a seventh embodiment using the example of a substrate of the third embodiment.

A detailed method is described below by way of example using a system with at least two culturing channels, for example a system as shown in FIG. 6, 7 or 8. All valves that are not described as opened are closed in the respective step. The method may comprise the following steps.

Cell seeding in the first culturing channel 2a: valve 18a is opened to the conduit, valve 15a is opened to the waste container, valve 17a is opened to the conduit. The applied pressure can for example be 20 mbar. The initial cell suspension flows from the storage container 12a through the conduit and the transfer channel into the culturing channel 2a. There, the cells sink to the floor and adhere. Cell division begins. Alternatively, valve 15a may be opened to the conduit and valve 17a may be opened to the waste container. The cells are then supplied directly (i.e. not via the transfer channel) to the culturing channel.

Washing away non-adherent and dead cells, for example 5 min to 60 min, particularly 20 min after cell seeding: valve 18b is opened towards the conduit, valve 15a is opened towards the waste container, valve 17a is opened towards the conduit. The applied pressure may be for example 50 mbar. Cell suspension is flushed through the culturing channel via the transfer channel to flush away non-adherent and dead cells. Alternatively, valve 15a can be opened to the conduit and valve 17a can be opened to the waste container. The cells then are directly (i.e. not via the transfer channel) transported away from the culturing channel from the substrate.

Trypsinization, for example when the cell culture has a predetermined cell density, for example after 48 hours: valve 18c is opened to the conduit, valve 15a is opened to the waste container, valve 17a is opened to the conduit. The applied pressure may be for example 20 mbar. Trypsin-containing solution flows from the storage container 12c through the transfer channel into the culturing channel 2a, remains there and detaches cells. The solution can have effect until a predetermined amount of cells is detached from the channel surface, for example about 5 minutes.

Cell transfer and concentrating: valve 18b is opened to the conduit, valve 15a is opened to the conduit, valve 16a is opened to the waste container. The applied pressure may be for example 100 mbar. Cell culture medium from the storage container 12b is pumped through the first culturing channel, the transfer channel, and the storage channel. For example, the volume of liquid supplied may be approximately 1.2 times the volume of the culturing channel. In the process, cells are transported through the transfer channel into the storage channel. Cells that are still attached to the surface of the culturing channel can be detached by the shear force and transferred as well. In the storage channel the cells can be retained for example by barriers, which may be formed in the form of a structuring of the floor of the storage channel or by a membrane at the access of the storage channel. Cell culture medium is transported away and cells remain in the storage channel.

Dilution: valve 18b is opened to the conduit, valve 16a is opened to the conduit, valve 17b is opened to the waste container. The applied pressure may be for example 20 mbar. Cell culture medium from the storage container 12b is transported out of the substrate through the storage channel and the transfer channel. In the process cells are transported out of the storage channel in a controlled manner. Depending on the duration or amount of liquid and flow velocity, the amount of cells remaining can be adjusted. For example, the volume of liquid supplied can be about two times the volume of the storage channel.

Optional mixing of liquid with the cells in the storage channel to obtain a more homogeneous cell distribution: for this purpose the liquid can be moved back and forth by applying positive and negative pressure. This step can be carried out before and/or after dilution.

Transfer to the and cell seeding in the second culturing channel 2b: valve 18b is opened to the conduit, valve 15b is opened to the waste container, valve 16a is opened to the conduit. The applied pressure may be for example 20 mbar. Cell culture medium from the storage container 12b transfers cells from the storage channel 6 via the transfer channel into the second culturing channel 2b. There, the cells sink to the floor and adhere. Cell division begins. Optionally, valve 17a may additionally be opened to the conduit and cell culture medium may be introduced into the substrate through transfer access 7a and combined with cells transferred from the storage channel during transfer of cells in the transfer channel, for example, to carry out dilution (alternatively or in addition to the aforementioned dilution in the storage channel).

Alternative to cell seeding in the second culturing channel: removal of the cells from the substrate.

The above sequence of steps can be repeated using another or the same storage channel for each repetition.

It is understood that features mentioned in the previously described embodiments are not limited to these particular combinations and are also possible in any other combinations.

What is claimed is:

1. A substrate for culturing cells, the substrate comprising:
a fluid channel system formed in the substrate, comprising:
a culturing channel for growing a cell culture, comprising a culturing access to an outside;
a storage channel for one or more selected from the group consisting of: storing, concentrating, homogenizing, and diluting a cell suspension containing transferred cells, comprising a storage access to the outside; and
a transfer channel with a transfer access to the outside, wherein the culturing channel and the storage channel are fluidically connected to each other via the transfer channel;
wherein at least one wall of the culturing channel, comprising at least a partial area of a floor and/or of side walls of the culturing channel, has a structuring which is configured in such a way that a growth surface is increased, the structuring comprising one or more selected from the group consisting of: a saw tooth profile, a wave profile, a lamellar structure, fibrous areas, and porous areas;
wherein the substrate is configured to:
receive an initial cell suspension through the culturing access into the culturing channel or through the transfer access via the transfer channel into the culturing channel;
grow a cell culture in the culturing channel;
transfer cells of the cell culture from the culturing channel into the storage channel via the transfer channel, wherein the transferring is to be carried out by supplying a transfer liquid through the culturing access, and transporting the transfer liquid through the culturing channel and the transfer channel into the storage channel; and
enable one or more selected from the group consisting of: storing, concentrating, homogenizing, and diluting a cell suspension containing the transferred cells in the storage channel.

2. The substrate according to claim 1, wherein:
the fluid channel system comprises at least one of a shape, an arrangement, an orientation, or a connection of the channels, that moves liquids through the fluid channel system on transport paths exclusively by one or more selected from the group consisting of: selectively opening and closing the accesses, and applying pressure to the fluid channel system.

3. The substrate according to claim 1, wherein:
the culturing channel, the storage channel and the transfer channel are arranged in one plane; or
a mouth of the culturing channel into the transfer channel is arranged along the transfer channel offset from a mouth of the storage channel into the transfer channel.

4. The substrate according to claim 1, wherein:
a longitudinal axis of the transfer channel is arranged at an angle substantially perpendicular to a longitudinal axis of the culturing channel.

5. The substrate according to claim 1,
wherein at least one of the culturing channel or the storage channel is narrowed towards the transfer channel.

6. The substrate according to claim 1, wherein:
at least one wall of the culturing channel, comprising at least a partial area of at least one of a floor, a ceiling or side walls of the culturing channel comprises a coating that promotes adhesion of cells, the coating selected from the group consisting of: a hydrophilic coating and a cell-adhering coating.

7. The substrate according to claim 1, wherein:
at least one wall of at least one of the transfer channel or the storage channel has a surface property that prevents growing-on of cells on the at least one wall.

8. The substrate according to claim 1, wherein:
a floor of the storage channel has a structuring configured in such a way that movement of cells lying on the floor is impeded, at least in one direction.

9. The substrate according to claim 1, wherein:
a longitudinal axis of the transfer channel is arranged at an angle greater than or equal to 50° with respect to a longitudinal axis of the culturing channel.

10. The substrate according to claim 1, wherein:
a longitudinal axis of the transfer channel is arranged at an angle greater than or equal to 75° with respect to a longitudinal axis of the culturing channel.

11. The substrate according to claim 1, wherein:
a longitudinal axis of the transfer channel is arranged at an angle greater than or equal to 85° with respect to a longitudinal axis of the culturing channel.

12. The substrate according to claim 1, wherein:
at least one wall of the culturing channel, comprising at least a partial area of at least one of a floor, a ceiling or side walls, is provided with a surface modification which is switchable with respect to its physical or chemical properties in such a way that switching causes detachment of the cells from the surface, wherein the surface modification comprises a thermoresponsive surface modification comprising a coating with poly-N-isopropylacrylamide (PNIPAM)-based polymers.

13. The substrate according to claim 1, wherein:
at least one wall of the culturing channel, comprising at least a partial area of a floor of the culturing channel, is provided with a regenerable surface modification which is configured in such a way that cell adhesion can be changed, activated and/or deactivated, via competitive inhibition.

14. The substrate according to claim 1, further comprising:
active components arranged exclusively outside the substrate, configured to move liquids in the fluid channel system.

15. The substrate according to claim 14, wherein by actuating the active components, one or more selected from the group consisting of the following is set:
which liquid is supplied to the fluid channel system,
a sequence of liquids supplied to the fluid channel system,
through which access, liquid is supplied to the fluid channel system,
through which access, liquid is taken from the fluid channel system,
a transport path of liquid in the fluid channel system,
a flow rate of liquid in the fluid channel system, and
when liquid is one or more selected from the group consisting of: supplied, transported further, and discharged.

16. The substrate according to claim 15, wherein the setting is carried out by one or more selected from the group consisting of:
establishing and/or interrupting connections between a liquid container in which the respective liquid is stored and the fluid channel system by automatically opening and/or closing valves and/or switching multiway valves, and applying a pressure suitable for transporting the respective liquid into the fluid channel system and/or in the fluid channel system by actuating pumps.

17. The substrate according to claim 1, wherein no active components, no measurement device, and no controller are arranged in the substrate.

18. The substrate according to claim 1, wherein the cells of the cell culture are detachable from walls of the culturing channel by one or more selected from the group consisting of: enzymatically and by shear forces arising during movement of a liquid in the culturing channel before they are transferred via the transfer channel into the storage channel.

19. The substrate according to claim 1, wherein:

the culturing channel is a first culturing channel and the transfer liquid is a first transfer liquid, and the fluid channel system comprises a second culturing channel fluidically connected to the transfer channel.

20. The substrate according to claim 19, wherein the substrate is configured such that the cells are to be transferred from the storage channel via the transfer channel into the second culturing channel by means of a second transfer liquid and an additional cell culture is to be grown by multiplying the cells in the second culturing channel.

21. A system comprising:

a substrate comprising:

a fluid channel system formed in the substrate, comprising:

a culturing channel for growing a cell culture, comprising a culturing access to an outside;

a storage channel for one or more selected from the group consisting of: storing, concentrating, homogenizing, and diluting a cell suspension containing transferred cells, comprising a storage access to the outside; and a transfer channel with a transfer access to the outside, wherein the culturing channel and the storage channel are fluidically connected to each other via the transfer channel;

wherein at least one wall of the culturing channel, comprising at least a partial area of a floor and/or of side walls of the culturing channel, has a structuring which is configured in such a way that a growth surface is increased, the structuring comprising one or more selected from the group consisting of: a saw tooth profile, a wave profile, a lamellar structure, fibrous areas, and porous areas;

wherein the substrate is configured to:

receive an initial cell suspension through the culturing access into the culturing channel or through the transfer access via the transfer channel into the culturing channel;

grow a cell culture in the culturing channel;

transfer cells of the cell culture from the culturing channel into the storage channel via the transfer channel, wherein the transferring is to be carried out by supplying a transfer liquid through the culturing access, and transporting the transfer liquid through the culturing channel and the transfer channel into the storage channel; and enable one or more selected from the group consisting of: storing, concentrating, homogenizing, and diluting a cell suspension containing the transferred cells in the storage channel;

at least three liquid containers arranged outside the substrate, wherein the culturing access, the storage access and the transfer access are each fluidically connected to at least one of the liquid containers; and active components, which are configured and arranged in such a way that, when actuated, they cause one or more selected from the group consisting of: a controlled supply of liquids from the liquid containers into the fluid channel system, or a controlled transport of liquids in the fluid channel system, and a controlled discharge of liquids from the fluid channel system, wherein the active components are arranged outside the substrate.

22. The system according to claim 21, wherein:

the at least three liquid containers comprise two storage containers for process liquids, and one waste container, and the culturing access is connected to one or more valves configured to establish a fluid connection between the culturing channel and at least one of the storage containers and to establish a fluid connection between the culturing channel and the waste container.

23. The system according to claim 21, further comprising:

one or more measurement devices arranged outside the substrate and configured to at least one of a) measure process measurands or b) optically inspect the cells in the substrate.

24. The system according to claim 21, further comprising:

a controller configured to control the active components, the controller being configured to regulate values of parameters to be set on the active components on a basis of target values and measured actual values of process measurands which are detected by a measurement device for measuring process measurands.

25. The system according to claim 21, wherein:

the at least three liquid containers comprise two storage containers for process liquids, and one waste container, and the culturing access is connected to two valves, one of which is configured to establish a fluid connection between the culturing channel and at least one of the storage containers, and the other of which is configured to establish a fluid connection between the culturing channel and the waste container.

26. The system according to claim 21, wherein:

the at least three liquid containers comprise two storage containers for process liquids, and one waste container, and the storage access is connected to a valve configured to establish a fluid connection between the storage channel and the waste container.

27. The system according to claim 21, wherein:

the at least three liquid containers comprise two storage containers for process liquids, and one waste container, and the transfer access is connected to a valve which is configured to establish a fluid connection between the transfer channel and the waste container.

28. The system according to claim 27, wherein the transfer access is connected to the valve or an additional valve, wherein the valve or the additional valve is configured to establish a fluid connection between the transfer channel and at least one of the storage containers.

29. The system according to claim 21, wherein:

a longitudinal axis of the transfer channel is arranged at an angle approximately perpendicular to a longitudinal axis of the culturing channel.

30. The system according to claim 21, wherein:

a longitudinal axis of the transfer channel is arranged at an angle greater than or equal to 50° with respect to a longitudinal axis of the culturing channel.

31. The system according to claim 21, wherein:

a longitudinal axis of the transfer channel is arranged at an angle greater than or equal to 75° with respect to a longitudinal axis of the culturing channel.

32. The system according to claim 21, wherein:

at least one wall of the culturing channel, comprising at least a partial area of at least one of a floor, a ceiling or side walls, is provided with a surface modification which is switchable with respect to its physical or chemical properties in such a way that switching causes detachment of the cells from the surface, wherein the surface modification comprises a thermoresponsive surface modification comprising a coating with poly-N-isopropylacrylamide (PNIPAM)-based polymers.

33. The system according to claim 21, wherein:

at least one wall of the culturing channel, comprising at least a partial area of a floor of the culturing channel, is provided with a regenerable surface modification which is configured in such a way that cell adhesion can be changed, activated and/or deactivated, via competitive inhibition.

34. The system according to claim 21, wherein by actuating the active components, one or more selected from the group consisting of the following is set:

which liquid is supplied to the fluid channel system, a sequence of liquids supplied to the fluid channel system, through which access liquid is supplied to the fluid channel system, through which access liquid is taken from the fluid channel system, a transport path of liquid in the fluid channel system, a flow rate of liquid in the fluid channel system, and when liquid is one or more selected from the group consisting of: supplied, transported further, and discharged.

35. The system according to claim 34, wherein the setting is carried out by one or more selected from the group consisting of:

establishing and/or interrupting connections between a liquid container in which the respective liquid is stored and the fluid channel system by automatically opening and/or closing valves and/or switching multiway valves, and applying a pressure suitable for transporting the respective liquid into the fluid channel system and/or in the fluid channel system by actuating pumps.

36. The system according to claim 21, wherein no active components, no measurement device, and no controller are arranged in the substrate.

37. The system according to claim 21, wherein the cells of the cell culture are detachable from walls of the culturing channel by one or more selected from the group consisting of: enzymatically and by shear forces arising during moving of a liquid in the respective culturing channel before they are transferred via the transfer channel into the storage channel.

38. The system according to claim 21, wherein:

the culturing channel is a first culturing channel and the transfer liquid is a first transfer liquid, and the fluid channel system comprises a second culturing channel fluidically connected to the transfer channel.

\* \* \* \* \*